(12) United States Patent
Pacetti et al.

(10) Patent No.: US 7,776,991 B2
(45) Date of Patent: *Aug. 17, 2010

(54) BIOLOGICALLY ABSORBABLE COATINGS FOR IMPLANTABLE DEVICES BASED ON POLYESTERS AND METHODS FOR FABRICATING THE SAME

(75) Inventors: Stephen D. Pacetti, San Jose, CA (US); Yiwen Tang, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/488,250

(22) Filed: Jun. 19, 2009

(65) Prior Publication Data
US 2009/0299007 A1 Dec. 3, 2009

Related U.S. Application Data

(63) Continuation of application No. 11/726,661, filed on Mar. 21, 2007, now Pat. No. 7,569,655, which is a continuation of application No. 10/996,765, filed on Nov. 24, 2004, now Pat. No. 7,214,759.

(51) Int. Cl.
*C08G 63/00* (2006.01)
*C08G 63/02* (2006.01)

(52) U.S. Cl. ........................ 528/190; 424/422; 424/423; 528/192; 528/193; 528/194

(58) Field of Classification Search ................. 424/422, 424/423; 528/190, 192, 193, 194
See application file for complete search history.

(56) References Cited

U.S. PATENT DOCUMENTS

| 4,032,993 A | 7/1977 | Coquard et al. |
| 4,049,748 A | 9/1977 | Bailey |
| 4,388,926 A | 6/1983 | Shalaby et al. |
| 4,419,507 A | 12/1983 | Sublett et al. |
| 5,563,223 A | 10/1996 | Tachika et al. |
| 6,331,313 B1 | 12/2001 | Wong et al. |
| 6,335,029 B1 | 1/2002 | Kamath et al. |
| 7,214,759 B2 * | 5/2007 | Pacetti et al. ................. 528/190 |
| 7,569,655 B2 * | 8/2009 | Pacetti et al. ................. 528/190 |

FOREIGN PATENT DOCUMENTS

| EP | 0 486 437 | 5/1992 |
| EP | 0 736 557 | 10/1996 |
| EP | 1 247 537 | 10/2002 |
| WO | WO 01/10929 | 2/2001 |
| WO | WO 03/080147 | 10/2003 |

OTHER PUBLICATIONS

Search Report for PCT/US2005/041997, filed Nov. 17, 2005, mailed May 3, 2006, 12 pgs.

* cited by examiner

*Primary Examiner*—Terressa M Boykin
(74) *Attorney, Agent, or Firm*—Squire Sanders & Dempsey, LLP

(57) ABSTRACT

The disclosure contains a medical article comprising a polymer containing polyesters and, optionally, agents for use with medical articles and methods of fabricating the same are disclosed. The medical article generally comprises an implantable substrate having a coating, and the coating contains a polymer comprising a polymeric product of a reaction comprising a polyol and a polycarboxylic acid.

12 Claims, No Drawings

BIOLOGICALLY ABSORBABLE COATINGS FOR IMPLANTABLE DEVICES BASED ON POLYESTERS AND METHODS FOR FABRICATING THE SAME

CROSS-REFERENCE TO RELATED APPLICATIONS

This is a continuation application of U.S. application Ser. No. 11/726,661, filed on Mar. 21, 2007, issued as U.S. Pat. No. 7,569,655, which is in turn a continuation application of U.S. application Ser. No. 10/996,765, filed on Nov. 24, 2004, issued as U.S. Pat. No. 7,214,759. The teachings in these two applications are incorporated herein by reference in their entirety.

BACKGROUND

1. Field of the Invention

This invention is directed to polymers for use with medical articles and, more specifically, polymers containing novel polyesters.

2. Description of the State of the Art

A current paradigm in biomaterials research is the use of bioabsorbable materials in medical implants. Bioabsorbable materials can be used, for example, as a reservoir for agents that can be therapeutic, prophylactic, diagnostic, or otherwise biologically beneficial. Such agents can be blended, mixed, connected or otherwise combined with the bioabsorbable material. In one example, a bioabsorbable material can serve as a reservoir for agents that create a non-fouling surface, which is a surface that does not become fouled or becomes less fouled with a layer of partially denatured proteins. Uncontrolled protein adsorption on an implant surface is a problem with currently available biomaterial implants and leads to such fouling on the implant surface that can also lead to disease, such as thrombosis, inflammation, a proliferative tissue response, or any combination of these diseases. A mechanism for the creation of diseases due to fouling may include, for example, providing cell-binding sites from adsorbed plasma proteins such as fibrinogen and immunoglobulin G. Platelets and inflammatory cells such as, for example, monocytes, macrophages and neutrophils adhere to the cell-binding sites. A wide variety of proinflammatory and proliferative factors may be secreted and result in disease.

Bioabsorbable materials can also be used to medicate implants by facilitating local administration of a therapeutic or prophylactic substance at a diseased site. A stent is an example of an implant that can be improved with a coating that can serve as a reservoir for the local administration of agents. As a mechanical intervention, stents can physically hold open and, if desired, expand a passageway within a mammal. Typically, a stent may be compressed, inserted into a lumen through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within the lumen of the coronary artery.

Local delivery of agents is often preferred over systemic delivery of agents, particularly where high systemic doses are necessary to achieve an effect at a particular site within a mammal, because high systemic doses of agent can often create adverse effects within the mammal. One proposed method of local delivery includes coating the surface of a medical article with a polymeric carrier that can be used as a reservoir for the delivery of agents. There are a large number of biodegradable polymers that have potential for such a use, and a polymer that is useful must be biocompatible, for example, in a vascular environment. The polymer must not elicit an adverse biological response greater than that elicited by stainless steel at all times until the polymer is absorbed. The biological response of a polymer is a complex function of polymer dose, degradation rate, acid generation, monomer compatibility, and response to morphological changes.

Bioabsorbable polymers can be categorized according to the type of labile linkage in the backbone of the polymer such as, for example, polyanhydrides, polyethers, polyesters, and the like. Currently used bioabsorbable polymers include poly (lactide), poly(glycolide), poly(lactide-co-glycolide) and poly(caprolactone), each of which are polyesters that are limited in their applications. For example, those of skill in the art know that poly(L-lactide) is quite strong but is inelastic, has a relatively high acid generation, and can present some biological response problems; and, poly(caprolactone) has a lower acid generation but is quite weak. Each of these polyesters undergo bulk erosion, which is less desirable for a coating material that is used to control release of agents.

Another problem involves regulatory concerns that may arise when agents attached to a polymeric coating remain attached to molecules from the polymeric coating upon degradation of the coating. Since these additional molecules were not considered in the original regulatory approval of the agent, there may be regulatory concerns over possible changes in the agent's biological activity.

Accordingly, there is a need for bioabsorbable polyesters that (i) have improved mechanical and biological response properties for applications that can benefit from such biodegradable polymers, and (ii) can release agents that are substantially free of additional molecules derived from a polymeric coating.

SUMMARY

Embodiments of the present invention generally encompass polymers containing polyesters and agents such as therapeutic, prophylactic or other agents, for use with medical articles. Methods for fabricating those polymers are also encompassed by the present invention.

In one embodiment, the invention is a composition comprising a polymer represented by the following formula:

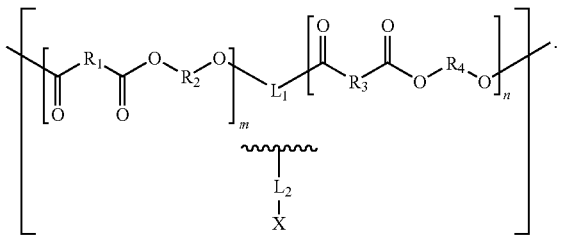

In this formula, the variables $R_1$ and $R_3$ are optional and each comprises a component independently selected from a group consisting of substituted, unsubstituted, hetero-, straight-chained, branched, cyclic, saturated and unsaturated aliphatic radicals; and substituted, unsubstituted, and hetero-aromatic radicals. The variables $R_2$ and $R_4$ each comprises a component independently selected from a group consisting of substituted, unsubstituted, hetero-, straight-chained, branched, cyclic, saturated and unsaturated aliphatic radicals; and substituted, unsubstituted, and hetero-aromatic radicals. The variable $L_1$ is an optional linkage, the variable X is an optional agent, the variable $L_2$ is an optional linkage connecting X to the polymer, and m and n are integers not equal to 0. In another embodiment, this composition is blended with an agent. In another embodiment, the invention is a stent comprising a coating that comprises the polymer, and the coating can be blended with an agent. In another embodiment, the invention is a medical article comprising a product of a reaction consisting of at least one polyol, at least one polycarboxylic acid, and optionally an agent.

In another embodiment, the invention is a method comprising fabricating a medical article or coating, wherein the medical article or coating comprises an implantable substrate, and the method further comprises preparing the polymer and forming the medical article or coating, wherein the medical article or coating comprises the polymer, the coating is formed on at least a portion of an implantable substrate, and the medical article or coating is optionally annealed. In another embodiment, the method can further comprise blending an agent with the composition comprising the polymer.

DETAILED DESCRIPTION

As discussed in more detail below, embodiments of the present invention generally encompass compositions including a polyester and an agent such as, for example, a therapeutic, prophylactic, diagnostic and/or other agent, for use with medical articles. The invention also encompasses methods for fabricating the compositions. The medical articles comprise any medical device such as, for example, an implantable medical device such as a stent. In some embodiments, the compositions can be used as a coating on the implantable substrate. In other embodiments, a medical device such as a stent is made in whole or in part from the composition. An "agent" can be a moiety that may be bioactive, biobeneficial, diagnostic, plasticizing, or have a combination of these characteristics. A "moiety" can be a functional group composed of at least 2 atoms, a bonded residue in a macromolecule, an individual unit in a copolymer or an entire polymeric block.

It is to be appreciated that any medical articles that can be improved through the teachings described herein are within the scope of the present invention. Examples of medical devices include, but are not limited to, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (AX-IUS™, Guidant Corp.) and endocardial leads (FINELINE® and ENDOTAK®, Guidant Corp.).

The medical devices can be comprised of a metal or an alloy, including, but not limited to, ELASTINITE® (Guidant Corp.); NITINOL® (Nitinol Devices and Components); stainless steel; tantalum; tantalum-based alloys; nickel-titanium alloy; platinum; platinum-based alloys such as, for example, platinum-iridium alloys; iridium; gold; magnesium; titanium; titanium-based alloys; zirconium-based alloys; alloys comprising cobalt and chromium (ELGILOY®, Elgiloy Specialty Metals, Inc.; MP35N and MP20N, SPS Technologies); or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

The Polymeric Compositions

The compositions of the present invention include mixtures, blends, and copolymers that comprise a polyester, which is biodegradable due to the labile nature of ester groups. Moreover, these compositions can be broken down, absorbed, resorbed and/or eliminated by a mammal.

For the purposes of the present invention, a polymer or coating is "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a mammal. It should be appreciated that traces or residue of polymer may remain on the device following biodegradation. The terms "bioabsorbable" and "biodegradable" are used interchangeably in this application. The polymers used in the present invention may be biodegradable and may include, but are not limited to, condensation copolymers.

A polyester of the present invention can comprise a reaction product of at least one polycarboxylic acid and at least one polyol. The polyesters can also contain a wide variety of other moieties and, as a result, can have a wide variety of molecular configurations. It should be appreciated that a polyester may comprise less than 100% of a biodegradable polymer such that polymers other than a polyester can compose the balance of composition. These other polymers can also be combined, mixed, blended or connected with the polyester; or, they can be cross-linked with the polyester using, for example, an isocyanate, a diisocyanate, diacyl halide, diene, or other cross-linking agent. The amount of these other polymers that are combined, mixed, blended, connected or cross-linked with the polyester should be limited by their effect on a required performance parameter of a product formed from the biodegradable polymer. Such performance parameters may include, for example, the mechanical strength of a coating, the biological response of the coating, or the rate of biodegradation and elimination of the coating from a mammal. If the other polymers are non-biodegradable, the polymer fragments produced during biodegradation should have molecular weights of a size that ensures elimination of the fragments from a mammal.

In some embodiments, the molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein.

Examples of polymers that can be combined, mixed, blended or connected with the PHAs of the present invention include, but are not limited to, poly(acrylates) such as poly (butyl methacrylate), poly(ethyl methacrylate), poly(hydroxyl ethyl methacrylate), poly(ethyl methacrylate-co-butyl methacrylate), copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly (vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly (phosphoester urethane); poly(trimethylene carbonate); poly (iminocarbonate); poly(ethylene); poly(propylene) co-poly (ether-esters) such as, for example, poly(dioxanone) and poly (ethylene oxide)/poly(lactic acid); poly(anhydrides), poly (alkylene oxalates); poly(phosphazenes); poly(urethanes); silicones; poly(esters); poly(olefins); copolymers of poly (isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly (carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof.

With respect to the chemical notation used herein, each of the functional groups, R, can be independently selected from substituted, unsubstituted, hetero-, straight-chained, branched, cyclic, saturated or unsaturated aliphatic radical; or a substituted, unsubstituted, or hetero-aromatic radicals. For example, an R group can be selected from H; aliphatic hydrocarbon groups such as, for example, alkyl, alkenyl, and alkynyl groups; aromatic groups such as, for example, aryl, aralkyl, aralkenyl, and aralkynyl groups; and, various other groups as defined below. In some embodiments of the present invention, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 6 to about 180 carbon atoms, from about 12 to about 150 carbon atoms, from about 18 to about 120 carbon atoms, from about 24 to about 90 carbon atoms, from about 30 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, iso-octyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms are replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain where at least one of the carbon-carbon linkages is a carbon-carbon double bond. The term "alkynyl" refers to a straight-chained or branched hydrocarbon chain where at least one of the carbon-carbon linkages is a carbon-carbon triple bond. The term "aryl" refers to a hydrocarbon ring bearing a system of conjugated double bonds often comprising at least six π (pi) electrons. Examples of aryl groups include, but are not limited to, phenyl, naphthyl, anisyl, toluyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of sidechains having 1 or more carbon atoms. In some embodiments, a radical is straight-chained if it has less than 0.01 mole percent of such sidechains. In other embodiments, a radical is straight-chained if it has less than 0.001 mole percent of such sidechains. A radical is "branched" when it has more than 0.1 mole percent of sidechains having 1 or more carbon atoms. In some embodiments, a radical is branched when it has more than 0.01 mole percent of such sidechains. In other embodiments, a radical is branched when it has more than 0.001 mole percent of such sidechains. The terms "radical," "group," "functional group," and "substituent" can be used interchangeably in some contexts and can be used together to further describe a chemical structure. For example, the term "functional group" can refer to a chemical "group" or "radical," which is a chemical structure variable that is in-chain, pendant or terminal to the chemical structure.

Examples of functional groups include, but are not limited to, ethers; esters; orthoesters; anhydrides, ketones; amides;

urethanes and their thio-derivatives (at least one oxygen atom is replaced by a sulfur atom); halogens; oxygen-containing groups such as, for example, hydroxyl, alkoxyl, epoxyl, carboxyl, and carbonyl; nitrogen-containing groups such as, for example, amino, amido, nitro, isocyanato, azido, diazo, hydrazino, azo, azoxyl, and cyano; sulfur-containing groups such as thio, sulfone, sulfoxide, and sulfido; and ethylenically unsaturated groups such as, for example, allyl, acryloyl and methacrylol, and maleate and maleimido. Such a functional group may be substituted. Examples of substituents in substituted radicals include, but are not limited to, alkyls, hydroxyls, carboxyls, aminos, amidos, iminos and combinations thereof. Such a functional group can also, for example, contain a heteroatom. Examples of heteroatoms of the heteroradicals include, but are not limited to, sulfur, phosphorous, oxygen, nitrogen and combinations thereof.

Biobeneficial and Bioactive Agents

The agents may be blended, mixed, connected, or otherwise combined with the polymers in the present invention. The agents can be biobeneficial, bioactive, diagnostic, plasticizing, or have a combination of these characteristics.

A "bioactive agent" is a moiety that can be mixed, blended, connected or otherwise combined with a polymer to provide a therapeutic effect, a prophylactic effect, both a therapeutic and a prophylactic effect, or other biologically active effect. The bioactive agents include, but are not limited to, small molecules, nucleotides, oligonucleotides, polynucleotides, amino acids, oligopeptides, polypeptides, and proteins. Moreover, the bioactive agents of the present invention may remain linked to a portion of the polymer or be released from the polymer.

A "biobeneficial agent" is an agent that can also be mixed, blended, connected or otherwise combined with a polymer to provide a biological benefit within a mammal without necessarily being released from the polymer. A polymer or coating can be modified with a biobeneficial agent, for example, (i) to be non-thrombogenic, such that protein absorption is inhibited or prevented to avoid formation of a thromboembolism; (ii) to promote healing such as, for example, through formation of a healthy and functional endothelial layer within a blood vessel by controlling endothelialization; or (iii) to be non-inflammatory, such as, for example, through the biobeneficial agent acting as a biomimic on the surface of an implant to passively avoid attracting monocytes and neutrophils, which can lead to a cascade of events and create an inflammation.

The biobeneficial agent can be blended, mixed, connected or otherwise combined with the polymer. A polymer or coating can be modified with a bioactive agent, for example, to inhibit the activity of vascular smooth muscle cells, or to control the migration or proliferation of smooth muscle cells to inhibit restenosis.

A "diagnostic agent" is a type of bioactive agent that can be used, for example, in diagnosing the presence, nature, or extent of a disease or medical condition in a mammal. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF) and microwave laser. Diagnostic agents may also include any other agents useful in facilitating diagnosis of a disease or other condition in a patient, whether or not imaging methodology is employed.

In some embodiments, the biobeneficial agents can be released or separate from the polymer. In other embodiments, the biobeneficial agents can have a reactive group that links the agent to the polymer. Examples of reactive groups include, but are not limited to, hydroxyl, carboxyl, and amino groups.

In some embodiments, the molecular weight of the agent should be at or below about 40,000 Daltons, or any range therein, to ensure elimination of the agent from a mammal. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein. If upon release, the biobeneficial agent is rapidly broken down in the body, then the molecular weight of the agent could be greater than about 40,000 Daltons without compromising patient safety. It is to be appreciated that one skilled in the art would recognize that some of the groups, subgroups, and individual biobeneficial agents may not be used in some embodiments of the present invention.

Examples of biobeneficial agents include, but are not limited to, many of the polymers listed above such as, for example, carboxymethylcellulose, poly(alkylene glycols), poly(N-vinyl pyrrolidone), poly(2-hydroxyethyl methacrylate), poly(3-hydroxypropyl methacrylamide), poly(acrylamide methyl propane sulfonic acid), poly(styrene sulfonate), sulfonated dextran, polyphosphazenes, poly(orthoesters), poly(tyrosine carbonate), dermatan sulfate, hyaluronic acid, heparin, chondroitan sulfate, glycosaminoglycans, chitin, chitosan, and any derivatives, analogs, homologues, congeners, salts, copolymers and combinations thereof.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin complexed with quaternary ammonium compounds, heparin sulfate, heparinoids, heparin-based compounds and heparin derivatized with hydrophobic materials.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof.

In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art would recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.). Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radioopaque materials and include, but are not limited to, materials comprising iodine or iodine-derivatives such as, for example, iohexal and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomography (PET).

Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

Plasticizing Agents

The terms "plasticizer" and "plasticizing agent" can be used interchangeably in the present invention, and refer to any agent, including any agent described above, where the agent can be added to a polymeric composition to modify the mechanical properties of the composition or the mechanical properties of a product formed from the composition. Plasticizers can be added, for example, to reduce crystallinity, lower the glass-transition temperature ($T_g$), or reduce the intermolecular forces between polymers, with a design goal that may include creating or enhancing mobility between polymers in the composition.

The mechanical properties that are modified include, but are not limited to, Young's modulus, tensile strength, impact strength, and tear strength. The plasticizer can be monomeric, polymeric, co-polymeric, or a combination thereof, and can be added to a polymeric composition with or without covalent bonding. Plasticization and solubility are analogous in that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and, any analogs, derivatives, copolymers and combinations thereof.

The molecular weights of the plasticizers can range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. The amount of plasticizer used in the present invention, can range from about 0.001% to about 70%; from about 0.01% to about 60%; from about 0.1% to about 50%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the present invention. For example, the plasticizers can be blended, mixed, connected, or otherwise combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

It should also be appreciated that the plasticizers can be blended, mixed, bonded, or otherwise combined with other active agents to obtain other desired functions such as, for example, an added therapeutic, prophylactic, and/or diagnostic function. In some embodiments, the plasticizers can be linked to other agents through ether, amide, ester, orthoester, anhydride, ketal, acetal, and all-aromatic carbonate linkages, which are discussed in more detail below.

It should also be appreciated that each of the agents of the present invention can have properties that are biobeneficial, bioactive, diagnostic, plasticizing or a combination thereof. For example, classification of an agent as a biobeneficial agent does not preclude the use of that agent as a bioactive agent, diagnostic agent and/or plasticizing agent. Likewise, classification of an agent as a bioactive agent does not preclude the use of that agent as a diagnostic agent, biobeneficial agent and/or plasticizing agent. Furthermore, classification of an agent as a plasticizing agent does not preclude the use of that agent as a biobeneficial agent, bioactive agent, and/or diagnostic agent.

It should also be appreciated that any of the foregoing agents can be mixed, blended or otherwise connected with the polymers of the present invention in any form such as, for example, in the form of a medical device or a coating for a medical device. By way of example, a stent coated with the polymers of the present invention can contain paclitaxel, docetaxel, rapamycin, ABT-578, or everolimus.

Concentrations of Agents

The agents of the present invention can be blended, mixed, connected, or otherwise combined with other agents to obtain other desired functions of the polymeric compositions. The amounts of the agents that compose the polymeric compositions vary according to a variety of factors including, but not limited to, the biological activity of the agent; the age, body weight, response, and the past medical history of the subject, the type of atherolscerotic disease, presence of systemic diseases such as diabetes; and, the pharmacokinetic and pharmacodynamic effects of the agents or combination of agents. Factors such as these are routinely considered by one of skill in the art when administering an agent to a mammal.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and, any range therein, where the percentage is based on the total weight of the polymer and agent or combination of agents.

Copolymers and Agents

The polyesters of the present invention can be connected to an agent in the formation of a polyester copolymer, wherein the agent can be a pendant group or an in-chain group. The present invention includes blends, mixtures and other combinations, but copolymers can offer stability in performance since, for example, some blends and mixtures can include agents that will leach at a rate that is faster than desired. An example of a composition that is improved through copolymerization is the combination of a PEG and a polyester. While not intending to be bound by any theory or mechanism of action, the formation of a copolymer can prevent the formation of discrete phases by phase separation that may otherwise occur in such a blend or mixture of hydrophobic and hydrophilic materials, allowing for a much higher concentration of a component such as, for example, PEG, to be added to a polyester to obtain a desired property.

In some embodiments, the compositions of the present invention can be designed for a predetermined degree of crystallinity that can be reproducible. While not intending to be bound by any theory or mechanism of action, the degree of crystallinity can affect the water swelling and hydrolytic lability of a polymer, thus affecting the bioabsorption rate and rate of release of an agent. In other embodiments, the compositions of the present invention can be designed to exhibit surface erosion rather than bulk erosion in order to, for example, provide a product, such as an agent-releasing stent or coating that may be considered more desirable in some applications.

A polymer of the present invention can comprise a polymeric carrier having an A-moiety (A), a B-moiety (B), and an optional linkage ($L_1$). The polymeric carrier may further comprise an optional agent (X), and an optional linkage ($L_2$) connecting X to the polymer. The polymer composition can be generally represented by the following formula (I):

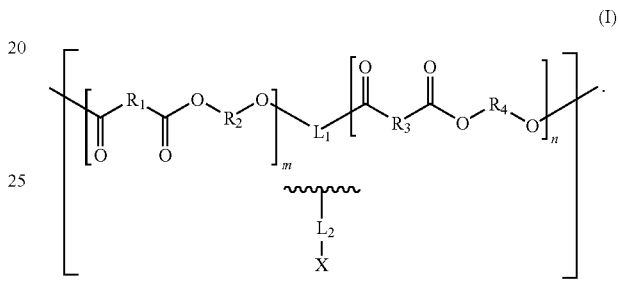

In formula (I), $R_1$ and $R_3$ are optional and independently selected from a group consisting of substituted, unsubstituted, hetero-, straight-chained, branched, cyclic, saturated and unsaturated aliphatic radicals; and substituted, unsubstituted, and hetero-aromatic radicals. $R_2$ and $R_4$ are independently selected from a group consisting of substituted, unsubstituted, hetero-, straight-chained, branched, cyclic, saturated and unsaturated aliphatic radicals; and substituted, unsubstituted, and hetero-aromatic radicals. $L_1$ is an optional linkage in the polymeric backbone, and X is an optional agent. $L_2$ is an optional linkage connecting X to the polymer, and m and n are integers not equal to 0.

In some embodiments, $L_1$ can comprise a substituted, unsubstituted, hetero-, straight-chained, branched, cyclic, saturated or unsaturated aliphatic radical; and a substituted or unsubstituted aromatic radical. In other embodiments, $L_1$ can comprise from about 0 to about 50 carbon atoms, from about 2 to about 40 carbon atoms, from about 3 to about 30 carbon atoms, from about 4 to about 20 carbon atoms, from about 5 to about 10 carbon atoms, and any range therein. In other embodiments, $L_1$ can comprise a non-carbon species such as, for example, a disulfide.

In other embodiments, $L_1$ can comprise poly(vinyl pyrrolidone); carboxymethylcellulose; poly(ethylene); polypropylene; hyaluronic acid, heparin, poly(styrene sulfonate), phosphorylcholine; substituted methacrylates; substituted or unsubstituted poly(alkylene glycols), which include, but are not limited to, PEG and PEG derivatives such as mPEG, amino-terminated PEG, or carboxyl terminated PEG; poly(propylene glycol), poly(tetramethylene glycol), poly(ethylene oxide-co-propylene oxide), poly(ethylene glycol-co-hydroxybutyrate), or copolymers and combinations thereof. In one embodiment, the poly(alkylene glycol) is PEG. In other embodiments, the poly(alkylene glycol) may comprise a PEG derivative such as mPEG. In other embodiments, $L_1$ can comprise a co-polymer of PEG or a copolymer of a PEG derivative, such as amino-terminated PEG. In other embodiments, $L_1$ can comprise a co-polymer of PEG and heparin, a copolymer of PEG and hirudin, or a combination thereof.

The optional agent X can be connected to the polymer by $L_2$, which can be any interunit linkage. The selection of $L_2$ allows for control of the relative strength or stability of the bond between X and the polymeric carrier as compared to the strength or stability of the bonds within the polymeric carrier. Such control allows for a controlled release of agents that are substantially free of attached molecules from the polymeric carrier. Furthermore, X can be biobeneficial, bioactive, diagnostic, plasticizing, or have a combination of these properties. The selection of $L_2$ is discussed in further detail below.

As described above, a polyester of the present invention comprises a reaction product of at least one polycarboxylic acid, or derivative thereof, and at least one polyol, or derivative thereof. The polyols used in the present invention may be organic compounds having two or more hydroxyl groups. In some embodiments, the polyols include, but are not limited to, compounds represented by the following formula (II):

wherein R can be a substituted, unsubstituted, hetero-, straight-chained, branched, cyclic, saturated or unsaturated aliphatic radical; or a substituted, unsubstituted, or heteroaromatic radical; and i is an integer.

In some embodiments, the polyols are diols. Examples of diols that can be used include ethylene glycol; 1,2-propanediol; 1,3-propanediol; 1,4-butanediol; 1,5-pentanediol; 1,6-hexanediol; 1,7-heptanediol; 1,8-octanediol; 1,9-nonanediol; 1,10-decanediol; 1,11-undecanediol; 1,12-dodecanediol; dihydroxyacetone; serinol; cyclohexanedimethanols such as, for example, 1,4-cis-cyclohexanedimethanol; and, combinations thereof. In other embodiments, the diols can be aromatic diols such as, for example, 1,4-benzenedimethanol (also known as p-phenylene dicarbinol or as p-xylene-α,α'-diol). In other embodiments, polyols such as glycerol, trimethylolpropane, pentaerythritol and sorbitol are useful as long as the possibility of forming a crosslink is considered. Polyols can be selectively polymerized by protecting one or more groups to prevent crosslinking, intentionally forming a crosslink, or using chemistry that is selective for particular reactive groups. In other embodiments, functional diols such as serinol and diacetone alcohol can also be used.

In other embodiments, R can be a substituted or unsubstituted poly(alkylene glycol), which includes, but are not limited to, poly(ethylene glycol) (PEG), poly(propylene glycol), poly(tetramethylene glycol), poly(ethylene oxide-co-propylene oxide), poly(ethylene glycol-co-hydroxybutyrate), or copolymers and combinations thereof. In one embodiment, the poly(alkylene glycol) is PEG. In other embodiments, the poly(alkylene glycol) is a PEG derivative such as amino-terminated PEG or carboxyl terminated PEG. In other embodiments, R can be a co-polymer of PEG or a copolymer of a PEG derivative such as amino-terminated PEG. The PEGs can have molecular weights ranging from about 100 Daltons to about 40,000 Daltons, from about 200 Daltons to about 20,000 Daltons, from about 300 Daltons to about 10,000 Daltons, from about 400 Daltons to about 5000 Daltons, from about 500 Daltons to about 2000 Daltons, or any range therein. It is to be appreciated that one skilled in the art would recognize that some of the groups, subgroups, and individual polyols may not be used in some embodiments of the present invention.

The polycarboxylic acids used in the present invention may be organic acids having two or more carboxyl groups. In some embodiments, the polycarboxylic acids are represented by the following formula (III):

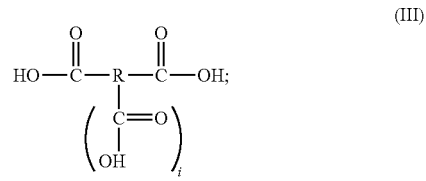

wherein R is optional and can be a substituted, unsubstituted, hetero-, straight-chained, branched, cyclic, saturated or unsaturated aliphatic radical; and a substituted or unsubstituted aromatic radical; and i is an integer.

Examples of polycarboxylic acids include, but are not limited to, oxalic acid, malonic acid, succinic acid, glutaric acid, adipic acid, pimelic acid, suberic acid, azelaic acid, sebacic acid, terephthalic acid, undecanedioic acid, dodecandioic acid, tridecanedioic acid, tetradecanedioic acid, pentadecanedioic acid, hexadecanedioic acid, citric acid, maleic acid, fumaric acid and combinations thereof. It is to be appreciated that one skilled in the art would recognize that some of the groups, subgroups, and individual polycarboxylic acids may not be used in some embodiments of the present invention.

In some embodiments, the polycarboxylic acids include dicarboxylic acids and tricarboxylic acids, either of which may be aliphatic or aromatic structures. In other embodiments, R comprises a methylene [—$(CH_2)_y$-] or phenylene radical [—$C_6H_4$—], where y is an integer between 0 and 16. In other embodiments, R may be substituted with an epoxy group. In other embodiments, R can include a substituted or unsubstituted poly(alkylene glycol), which includes, but is not limited to, PEG and PEG derivatives such as amino-terminated PEG or carboxyl-terminated PEG; poly(propylene glycol); poly(tetramethylene glycol), poly(ethylene oxide-co-propylene oxide); poly(ethylene glycol-co-hydroxybutyrate); or copolymers and combinations thereof. In one embodiment, the poly(alkylene glycol) is PEG. In another embodiment, the poly(alkylene glycol) is a PEG derivative such as an amino-terminated-PEG. In another embodiment, R can be a co-polymer of PEG or a copolymer of a PEG derivative such as amino-terminated-PEG.

In other embodiments, the aromatic dicarboxylic acids can be isomers of phthalic acid such as, for example, terephthalic acid, isophthalic acid, phthalic acid, and combinations thereof. In other embodiments, the phenyl ring of the aromatic dicarboxylic acid can be substituted with other groups such as alkyl groups, alkoxy groups, halogen groups, and any other functional groups defined above that will not interfere with polymerization.

As with the polyols, care must be taken to control crosslinking when using polycarboxylic acids to produce the polyesters of the present invention, because crosslinking can produce a polymer that has a high viscosity, is gelled, or is otherwise difficult to process. In some embodiments, crosslinking can be controlled by selecting polycarboxylic acids that contain carboxyl groups with different reactivities. In other embodiments, crosslinking can be controlled by protecting one or more of the carboxyl groups with a chemical moiety, such as, for example, by forming benzyl esters. In some embodiments, the polycarboxylic acids include, but are not limited to, 1,3,5-benzenetricarboxylic acid, tricarballylic acid, trimellitic acid and trimellitic anhydride. For example, combining trimellitic anhydride in a reaction with one equivalent of an amine or hydroxy functional compound can essentially functionalize, or protect, one of the carboxyl groups.

The polyesters can be formed by reacting at least one diol, or derivative thereof, with at least one dicarboxylic acid, or derivative thereof. In one embodiment, two equivalents of a diol can be combined with two equivalents of a dicarboxylic acid, and an acid catalyst. Examples of acid catalysts include, but are not limited to, p-toluenesulfonic acid, trifluoromethanesulfonic acid, and sulfuric acid. The mixture can be dissolved in a suitable solvent such as, for example, toluene or chlorobenzene. The mixture is then heated to reflux and the water generated is removed by azeotropic distillation using a Dean-Stark trap.

In another embodiment, two equivalents of a diol can be reacted with two equivalents of a diacylhalide under anhydrous conditions. The generated hydrochloric acid is neutralized using a non-nucleophilic base such as, for example, pyridine or triethylamine. In another embodiment, two equivalents of a diol can be reacted with two equivalents of a dianhydride derivative of a dicarboxylic acid. In one example, the dianhydride of acetic acid can be used, and the acetic acid formed during polymerization can be removed by distillation.

In another embodiment, two equivalents of a diol and two equivalents of a dicarboxylic acid ester can be polymerized by transesterification using Lewis acid type catalysts such as aluminum trichloride, titanium tetrachloride, titanium tetrabutoxide, and zinc chloride. In one example, titanium tetrabutoxide can be combined with the diols and dicarboxylic acid esters at a level of 0.025 to 0.25% (w/w), and the reaction mixture is heated to a temperature ranging from about 140° C. to about 260° C. while simultaneously applying a vacuum of at least about $10^{-2}$ bar to remove the liberated alcohol. In some embodiments, the vacuum can range from about $10^{-2}$ bar to about $10^{-5}$ bar.

Various combinations of diols and dicarboxylic acid can be used. In one embodiment, two equivalents of one diol can be used. In another embodiment, a mixture of one equivalent of one diol with one equivalent of another diol can be used. In another embodiment, two equivalents of one dicarboxylic acid can be used. In another embodiment, a mixture of one equivalent of one dicarboxylic acid and one equivalent of another dicarboxylic acid can be used. In any embodiment, the dicarboxylic acids can be aliphatic, aromatic, or a combination thereof.

In some embodiments, a family of polyesters can be represented by the following formula (IV):

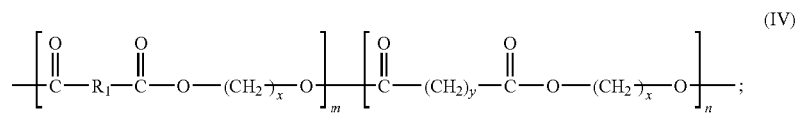

wherein $R_1$ is a phenylene radical such as, for example, a p-, m-, or o-phenylene; x is an integer ranging from about 2 to about 20, from about 3 to about 12, from about 4 to about 8, or any range therein; y is an integer ranging from about 0 to about 16, from about 1 to about 12, from about 2 to about 8, or any range therein; m is an integer ranging from about 5 to about 2250, from about 10 to about 2000, from about 15 to about 1500, from about 20 to about 1000, or any range therein; and, n is an integer ranging from about 5 to about 2900, from about 10 to about 2500, from about 15 to about 2000, from about 20 to about 1500, or any range therein.

In one embodiment, a polyester can be represented by the following formula (V):

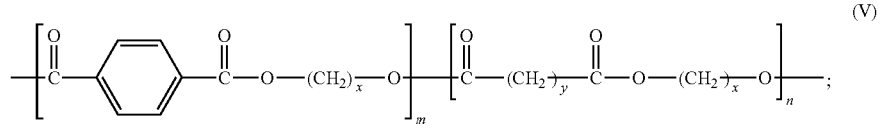

wherein one dicarboxylic acid is terephthalic acid, and the integers x, y, m and n are defined above.

In another embodiment, a polyester can be represented by the following formula (VI):

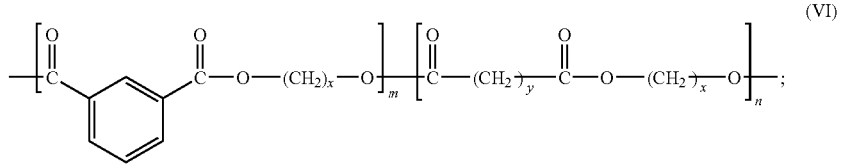

wherein one dicarboxylic acid is isophthalic acid; and the integers x, y, m and n are defined above.

In another embodiment, a polyester can be represented by the following formula (VII):

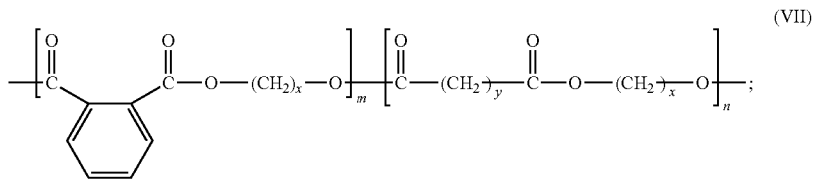

wherein one dicarboxylic acid is phthalic acid; and the integers x, y, m and n are defined above.

In another embodiment, a polyester can be represented by the following formula (VIII):

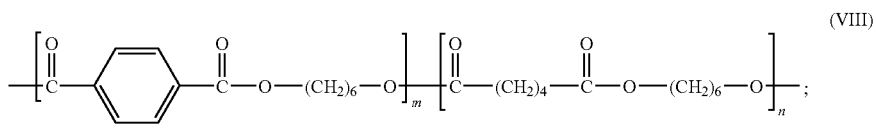

wherein one dicarboxylic acid is terephthalic acid, another dicarboxylic acid is adipic acid; and the polyol is 1,6-hexanediol.

As described above, the polyesters are formed by reacting particular diols and diacids in chosen molar ratios. Examples of combinations of particular diols and diacids include, but are not limited to, 1,3-propanediol, terephthalic acid and adipic acid in a molar ratio of 2:1:1, respectively; 1,4-butanediol, terephthalic acid and sebacic acid in a molar ratio of 2:1:1, respectively; and 1,6-hexanediol, terephthalic acid and adipic acid in molar ratios of either 2:1:1 or 2:0.5:1.5, respectively.

I. Agents Attached to the Polymer

There are a variety of ways in which agents can be combined with the polymers of the present invention. The agents can be linked ionically, by hydrogen bonding, via metal ion coordination, or covalently, or by physical interlinking with the polymer. In some embodiments, the $R_1$ through $R_4$, $L_1$, $L_2$, and/or X can be chemically functionalized to provide functional groups that are necessary for connecting agents as pendant groups to the polymer. Examples of functional groups that can be used in forming the connections are described above.

In some embodiments, the functional groups introduced to $R_1$ through $R_4$, $L_1$, $L_2$, and/or X include, but are not limited to, carboxylic acids, amines, thiols, alcohols, anhydrides, esters, other unsaturated groups and halogens. In other embodiments of the present invention, diacids comprising epoxy groups may be used to produce the polyesters, since epoxy groups are highly-strained reactive groups that can be used to connect agents to the polymer. Examples of such diacids may include, but are not limited to, 2,3-epoxysuccinic acid, 3,4-epoxyadipic acid or a diepoxyadipic acid.

Surface treatments can be used to localize the placement of agents on the polymer surface and include, for example, chemical, mechanical, and combined chemical and mechanical treatments, which are known to one of skill in the art. Mechanical surface treatment includes, but is not limited to, abrading, polishing, and applying laser energy to the surface. Laser surface treatment includes applying laser energy to heat, oxidize, pyrolyze, activate, or cleave chemical bonds. Chemical surface treatment includes, but is not limited to, etching such as, for example, chromic acid etching; ozonation; iodine treatment; sodium treatment; surface grafting; anodizing; thermal, flame, UV, corona discharge, and plasma treatments; and the use of primers. In some embodiments, medical articles may be surface treated after they have been formed, which can reduce problems that may be associated with using functionalized polyesters to form a medical article.

In some embodiments, the surface treatment comprises chromic acid etching to introduce functional groups such as, for example, hydroxyl, carbonyl, carboxylic acid, and —$SO_3H$ groups and form root-like cavities which provide sites for mechanical interlocking. In other embodiments, the surface treatment comprises applying a more aggressive etching solution containing, for example, a sodium-naphthalene complex dissolved in tetrahydrofuran or a sodium-ammonia complex dissolved in ammonia to introduce unsaturated bonds, carbonyl groups, and carboxyl groups. In other embodiments, the surface treatment comprises iodine treatment to alter the crystallinity of the polymer surface from an alpha form (where the N—H groups lie parallel to the surface) to a beta form (where the N—H groups stand perpendicular to the surface). In other embodiments, the surface treatment comprises application of a primer, which is typically a multifunctional chemical, to act as a chemical bridge between the polymer and an agent.

In some embodiments, the surface treatment comprises surface grafting a chemical to a polymeric surface to provide functional groups for attachment of an agent such as, for example, exposing a poly(ethylene) to gamma radiation in the presence of a vinyl acetate monomer to chemically graft the vinyl acetate monomer on the poly(ethylene) surface. In other embodiments, the surface treatment comprises plasma treatment with ions of a gas such as, for example, Ar, He, $N_2$, $O_2$, Air, and $NH_3$ to introduce functional groups such as, for example, carboxylic or amino groups. In other embodiments, the surface treatment comprises a corona discharge, usually in the presence of air and at atmospheric pressure, to introduce functional groups such as, for example, carbonyl, hydroxyl, hydroperoxide, aldehyde, ether, ester, and carboxylic acid groups, as well as unsaturated bonds.

In some embodiments, the surface treatment comprises flame treatment to oxidize the polymer surface and introduce functional groups such as, for example, hydroxyl, carbonyl, carboxyl, and amide groups through a free radical mechanism. In other embodiments, the surface treatment comprises thermally treating a polymeric surface with a blast of hot air (approximately 500° C.) to create functional groups such as, for example, carbonyl, carboxyl, amide, and hydroperoxide groups through a free radical mechanism. In other embodiments, the surface treatment comprises applying high-intensity ultraviolet (UV) radiation of a predetermined wavelength to create functional groups, where the process may use, for example, a wavelength of 184 nm to crosslink the surface of a polyethylene or a wavelength of 253.7 nm to avoid cross-linking and induce hydrogen bonding. In other embodiments, the surface treatment comprises abrading or polishing the polymer surface in the presence of an agent to create free radicals that react directly with the agent.

The selection of functional groups for connecting an agent to a polymer will affect the ability of the agent to release from the polymer in vivo. In formula (X), for example, $L_2$ is an ester, which may be undesirable in some embodiments. As illustrated and described below, the careful selection of $L_2$ can help alleviate safety and regulatory issues that may arise from the creation of derivatives of agent during biodegradation of the polymers.

In some embodiments, $L_2$ can be an ether, an amide, an imine, an ester, an oxime, an anhydride, an orthoester, an all-aromatic carbonate, an acetal, a ketal, a urethane, a urea, a glycoside, a disulfide, a siloxane linkage, or a combination thereof. In other embodiments, $L_2$ can include, but is not limited to, amides, ureas, urethanes, esters, semicarbazones, imines, oximes, anhydrides, ketals, acetals, orthoesters, disulfides, and all-aromatic carbonates. In some embodiments, $L_2$ can be an ester, an anhydride, a ketal, an acetal, an orthoester, or an all-aromatic carbonate. In some embodiments, $L_2$ can be an anhydride, a ketal, an acetal, an orthoester or an all-aromatic carbonate. In some embodiments, $L_2$ can be a ketal, an acetal, an orthoester or an all-aromatic carbonate. In some embodiments, $L_2$ can be an acetal, an orthoester or an all-aromatic carbonate. In some embodiments, $L_2$ can be an orthoester or an all-aromatic carbonate. In some embodiments, $L_2$ can be an all-aromatic carbonate such as, for example, the structure represented by formula (IX):

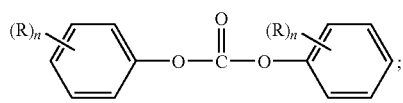

(IX)

wherein R is optional and can be independently selected from, for example, a substituted, unsubstituted, hetero-, straight-chained, branched, cyclic, saturated and unsaturated aliphatic radicals; substituted and unsubstituted aromatic radicals; and combinations thereof. The subscript n is an integer.

In some embodiments, the polyester can be represented by the following formula (X):

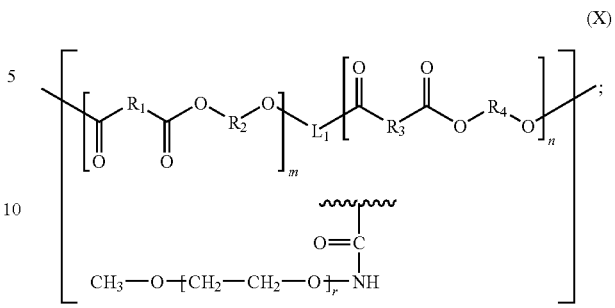

(X)

wherein $R_1$ through $R_4$, $L_1$, m and n are defined above; and r is an integer ranging from about 1 to about 100, from about 2 to about 80; from about 3 to about 70, from about 4 to about 60, from about 2 to about 20, from about 3 to about 30, from about 4 to about 40, from about 5 to about 50, and any range therein.

In formula (X), the agent is mPEG. The mPEG can be connected to any functional group. For example, $R_1$ through $R_4$ and $L_1$ can comprise a functionality that results in the creation of an amide linkage with the mPEG. An amide linkage can be considered a stable linkage relative to the stability of the remainder of the polymer. The amide linkage results from the conjugation of an amine-terminated mPEG with a carboxyl group present on any of $R_1$ through $R_4$ and $L_1$.

In some embodiments, the polyester can be represented by the following formula (XI):

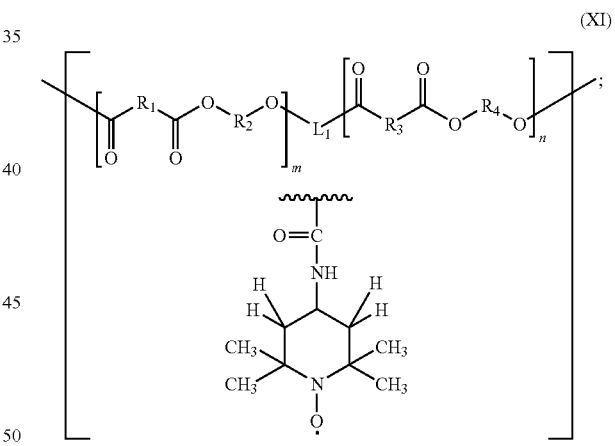

(XI)

wherein $R_1$ through $R_4$, $L_1$, m and n are defined above.

In formula (XI), the agent is 4-amino-2,2,6,6-tetramethylpiperidine-1-oxyl (4-amino-TEMPO). The 4-amino-TEMPO is connected to any of $R_1$ through $R_4$ and $L_1$ through an amide linkage, which may remain intact during biodegradation of the polymer resulting in attachment of additional molecules to the 4-amino-TEMPO that were derived from degradation of the polymer. As a result, a derivative of 4-amino-TEMPO can be released from the polymer rather than 4-amino-TEMPO and may cause regulatory concerns. The amide linkage results from the conjugation of 4-amino-TEMPO with a carboxyl group present on any of $R_1$ through $R_4$ and $L_1$.

In some embodiments, the polyester can be represented by the following formula (XII):

(XII)

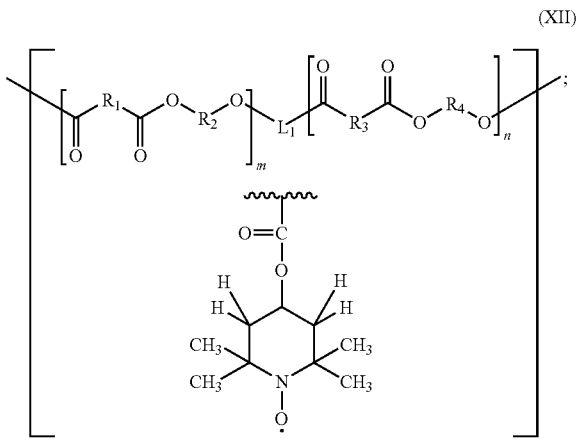

wherein $R_1$ through $R_4$, $L_1$, m and n are defined above.

In formula (XII), the agent is 4-hydroxy-2,2,6,6-tetramethylpiperidine-1-oxyl (4-hydroxy-TEMPO). The 4-hydroxy-TEMPO is connected to any of $R_1$ through $R_4$ and $L_1$ through an ester linkage, which is more labile than an amide linkage and allows for release of the agent from the polymer. The cleavage of the $L_2$ ester competes with the cleavage of the polyesters and may result in attachment of additional molecules to the 4-hydroxy-TEMPO that were derived from degradation of the polymer at ester linkages. The ester linkage results from the conjugation of a 4-hydroxy-TEMPO with a carboxyl group present on any of $R_1$ through $R_4$ and $L_1$.

In some embodiments, the polyester can be represented by the following formula (XIII):

(XIII)

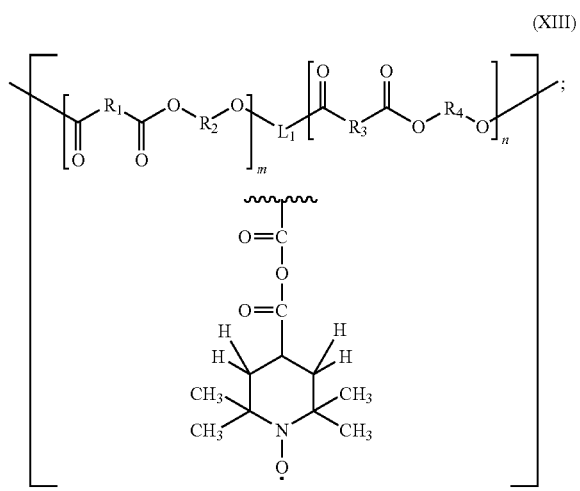

wherein n and m are integers not equal to 0.

In formula (XIII), the 4-carboxy-2,2,6,6-tetramethylpiperidine-1-oxyl (4-carboxy-TEMPO) is connected to any of $R_1$ through $R_4$ and $L_1$ through an anhydride linkage, which is more labile than an ester linkage and, thus, may allow for release of the agent without attachment of additional molecules derived from biodegradation of the polymer.

In some embodiments, a polyester is represented by the following formula (XIV):

(XIV)

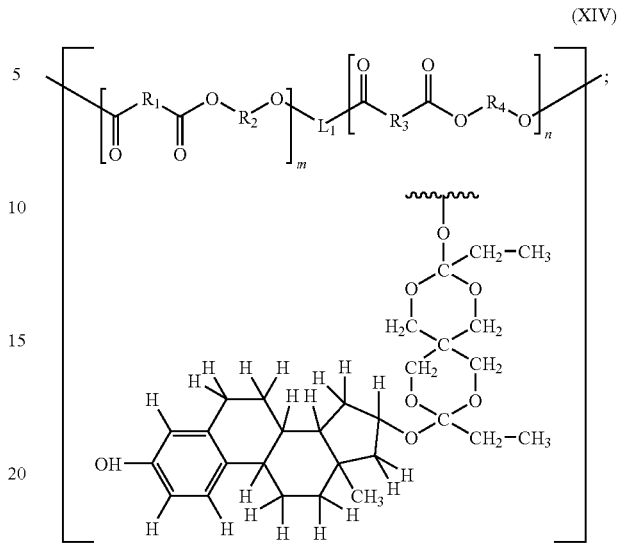

wherein n and m are integers not equal to 0.

In formula (XIV), the agent is estradiol and is connected to any of $R_1$ through $R_4$ and $L_1$ through an orthoester known as 3,9-diethylidene-2,4,8,10-tetraoxaspiro-[5,5]-undecane (DETOSU), which is a more labile ester.

To make the polymer in formula (XIV), a hydroxy-functional polyester can be used. Estradiol can be combined with DETOSU to form an estradiol-DETOSU combination. The hydroxy-functional polyester can be reacted with the estradiol-DETOSU combination to form the polyester-agent combination.

A polymeric agent such as, for example, heparin can be connected to a polyester as a graft-copolymer by conjugating an amino-functionalized polyester with an aldehyde-functionalized-heparin. The amino-functionalized polyester and aldehyde derivatized can be coupled by reductive amination using sodium cyanoborohydride ($NaCNBH_3$) and a DMF/water solvent.

II. Agent as a Polymeric Block

A polymeric agent can be connected to a polyester as a block-copolymer. Examples of agents that can be incorporated into polyesters as polymeric blocks include, but are not limited to, carboxymethylcellulose; poly(alkylene glycols) such as, for example, poly(ethylene glycol); phosphorylcholine functional methacrylates, poly(N-vinyl pyrrolidone), phosphorylcholine, poly(ethylene oxide), poly(acrylamide methyl propane sulfonic acid), poly(styrene sulfonate), sulfonated dextran; polyphosphazenes, poly(orthoesters), poly(tyrosine carbonate), glycosaminoglycans, amino acids such as, for example, the binding sequence RGD, oligopeptides, proteins such as, for example, elastin, collagen, and chondroitin sulfate; dermatan sulfate; hyaluronic acid; heparin; and any derivatives, analogs, homologues, congeners, salts, copolymers and combinations thereof.

1. Polyesters Comprising Glycosaminoglycans

A graft polymer of a polyester and a glycosaminoglycan such as heparin or hyaluronic acid, or a polyester with an endblock of a glycosaminoglycan such as heparin or hyaluronic acid, can be prepared by combining an amino functional or an amino-terminated polyester with an aldehyde-functionalized heparin. An example of a aldehyde-functionalized heparin is represented by the following formula (XV):

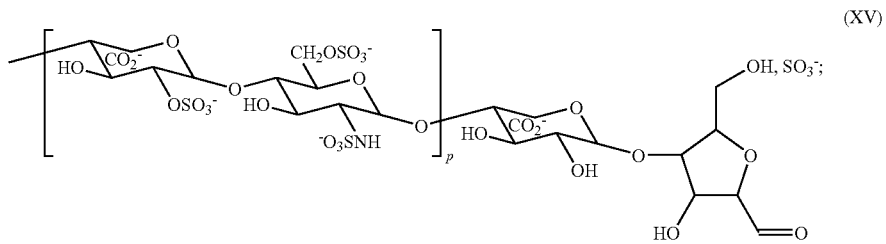

wherein p is an integer not equal to 0.

The aldehyde-functionalized heparin can be combined with an amino functional, or an amino-terminated polyester in a DMF/water solvent and subsequently reduced with NaCNBH$_3$ to produce the following polyester-heparin copolymer structure represented by formulas (XVI) and (XVII):

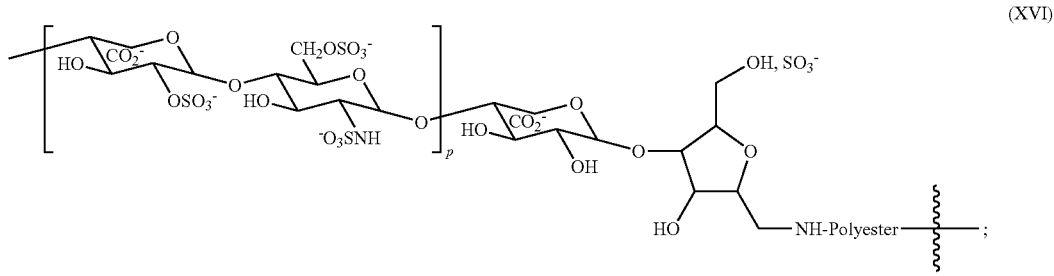

wherein p is an integer not equal to 0; and

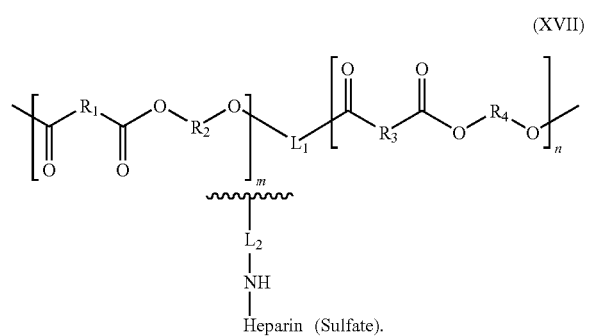

The polyester-heparin copolymer shown above is an AB-block copolymer. The AB-type copolymers result when the two polymers only have a single active end. The method of the present invention can be designed to produce copolymers such as graft copolymers, an AB copolymer, an ABA copolymer, or an ABABAB . . . multi-block copolymer by activating either one or both ends of the agent polymer and the polyester. Copolymers of the ABA-type result where one polymer has one active end and the other polymer has two active ends. Copolymers of the ABABAB . . . -type result where both polymers have two active ends. In one embodiment, the copolymer is an ABA copolymer where the A blocks are a glycosaminoglycan such as heparin or hyaluronic acid. In another embodiment, the copolymer is a graft copolymer comprising a glycosaminoglycan such as heparin or hyaluronic acid.

A block-copolymer of polyester and heparin can be prepared by combining a carboxyl-terminated polyester with a hydrazide-derivatized heparin in the presence of a coupling agent, such as a carbodiimide. The heparin is first activated with, for example, 1-ethyl-3-(3-dimethylaminopropyl)-carbodiimide (EDC) or dicyclohexylcarbodiimide (DCC) and then combined with a large excess of adipic dihydrazide to prepare an amino-functionalized heparin which is then coupled to the terminal carboxy group on the polyester. Alternatively, an aldehyde-functionalized heparin can be treated with ammonia or n-butylamine in the presence of a reducing agent such as, for example, sodium borohydride (NaBH$_4$), potassium borohydride (KBH$_4$), or NaCNBH$_3$. The carboxyl-terminated polyester can be activated with, for example, EDC or DCC, and combined with the amino-functional heparin.

An AB or ABA block-copolymer of polyester and heparin can be prepared by combining a carboxyl-terminated polyester with heparin and reacting the carboxy group with a heparin hydroxyl group. The polyester is first combined with an excess of diacid to prepare the carboxyl-terminated polyester. Alternatively, a polyester with hydroxyl end-groups can be oxidized with Ag$_2$O, H$_2$O$_2$, KMnO$_4$, CrO$_3$, or a peroxy acid to form a carboxyl-terminated polyester. The carboxyl-terminated polyester can be activated with, for example, EDC or DCC, and then combined with the heparin.

In some embodiments of the present invention, the agent may be any biobeneficial agent that can enhance the biocompatibility or non-fouling properties of a polyester. For example, hyaluronic acid can be a polymeric agent used to form a polyester-hyaluronic acid graft or other copolymer. Hyaluronic acid has free carboxyl groups to provide the functionality for a link, or an aldehyde-functionalized hyaluronic acid can be made, for example, by oxidizing hyaluronic acid with nitrous acid or periodate. The aldehyde-functionalized hyaluronic acid can then be combined with a polyester as described above.

The polyesters of the present invention can be combined with many different moieties and, thus, can have multiple functionalities. A polyester can be analyzed, for example, using standard analytical techniques to determine a ratio of carboxyl groups to hydroxyl groups. The same is true of a polyester that also contains other functionalities such as, for example, amino functionality. Knowing the ratio of functionalities will allow one skilled in the art to decide whether to connect the polymer agent to the hydroxyl ends, the amino ends, or the carboxyl ends of the polyester. A skilled artisan can protect groups on the polyester such as amino groups, for example, with benzyl chloroformate to reduce undesirable side conjugation when combining a carboxyl-terminated polyester with a hydrazide-derivatized heparin.

2. Polyester-Poly(ethylene glycol) Block Copolymers

A block copolymer of a polyester and PEG can be prepared using a variety of techniques. In one embodiment, a hydroxyl-terminated polyester can be combined with a carboxyl-terminated PEG (Nektar Corp.) in the presence of, for example, EDC or DCC to form the following structure represented by the following formula (XVIII):

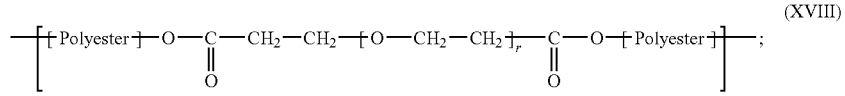

(XVIII)

wherein r can range from about 1 to about 100, from about 2 to about 80; from about 3 to about 70, from about 4 to about 60, from about 2 to about 20, from about 3 to about 30, from about 4 to about 40, from about 5 to about 50, and any range therein.

In another embodiment, an amino-terminated polyester can be combined with a carboxyl-terminated PEG (Nektar Corp.) in the presence of, for example, EDC or DCC. In another embodiment, either a succinimidyl derivative of mPEG (Nektar Corp.) or an isocyanate-terminated mPEG (Nektar Corp.) can be reacted with an amino-terminated polyester under conditions known to those of skill in the art. In another embodiment, the carboxyl group of a carboxyl-terminated polyester can be activated with, for example, EDC or DCC and combined with an amino-terminated mPEG (Nektar Corp.) In another embodiment, an amino-terminated mPEG can be combined with a high molecular weight polyester in the presence of a base catalyst through amination of ester groups in a high molecular weight polyester. In another embodiment, an amino-terminated polyester can be combined with a methacrylate-terminated mPEG (Nektar Corp.) in the presence of an initiator capable of undergoing thermal or photolytic free radical decomposition. Examples of suitable initiators include benzyl-N,N-diethyldithiocarbamate or p-xylene-N,N-diethyldithiocarbamate. In another embodiment, an amino-terminated polyester can be combined with ethylene oxide in a living polymerization reaction that forms a PEG block, and which is an unterminated anionic polymerization kept alive and controlled by maintaining a pure system. A living polymerization reaction can be stopped through addition of a terminating agent such as, for example, water.

Forming a Coating

In some embodiments of the invention, the compositions are in the form of coatings for medical devices such as, for example, a balloon expandable stent or a self expanding stent. There are many coating configurations within the scope of the present invention, and each configuration can include any number and combination of layers. In some embodiments, the coatings of the present invention can comprise one or a combination of the following four types of layers:

(a) an agent layer, which may comprise a polymer and an agent or, alternatively, a polymer free agent;

(b) an optional primer layer, which may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

In one embodiment, the agent layer can be applied directly to at least a part of an implantable substrate as a pure agent to serve as a reservoir for at least one bioactive agent. In another embodiment, the agent can be combined with a biodegradable polymer as a matrix, wherein agent may or may not be bonded to the polymer. In another embodiment, the optional primer layer can be applied between the implantable substrate and the agent layer to improve adhesion of the agent layer to the implantable substrate and can optionally comprise an agent. In another embodiment, a pure agent layer can be sandwiched between layers comprising biodegradable polymer. In another embodiment, the optional topcoat layer can be applied over at least a portion of the agent layer to serve as a membrane to control the rate of release of the bioactive agent and can optionally comprise agent. In another embodiment, the biocompatible finishing layer can also be applied to increase the biocompatibility of the coating by, for example, increasing acute hemocompatibility and can also comprise an agent.

The inventive compositions can be used for one or any combination of layers. In addition, in some embodiments, other polymers such as those previously mentioned (e.g., poly(butyl methacrylate), etc.) can be used as one of the layers or can be blended or crosslinked with the polyester embodiments.

Each layer can be applied to an implantable substrate by any method including, but not limited to, dipping, spraying, pouring, brushing, spin-coating, roller coating, meniscus coating, powder coating, inkjet-type application or a combination thereof. In one example, each of the layers can be formed on a stent by dissolving one or more biodegradable polymers, optionally with a non-biodegradable polymer, in one or more solvents and either (i) spraying the solution on the stent or (ii) dipping the stent in the solution. In this example, a dry coating of biodegradable polymer may be formed on the stent when the solvent evaporates.

The formation of each layer may involve use of a casting solvent. A casting solvent is a liquid medium within which a polymer can be solubilized to form a solution that may be applied on a substrate. The casting solvent must be selected to avoid adversely affecting an underlying material such as, for example, an underlying primer layer or a bare stent structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, hydrogen bonding, molecular size, volatility, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory.

It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Exemplary casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30° C. to about 200° C., from about 35° C. to about 190° C., from about 40° C. to about 180° C., from about 45° C. to about 175° C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

The following examples are provided to further illustrate embodiments of the present invention.

Example 1

Synthesis of Co-poly-{[Hexyleneterephthalate]$_{22}$-[Hexylenesebacinate]$_{78}$}

Dimethylterephthalate (15.65 g, 0.0807 mole), 1,6-hexanediol (42.76 g, 0.3624 mole), dimethylsebacate (64.79 g, 0.2817 mole), and titanium tetrabutoxide (0.1 g, 2.94×10$^{-4}$ mole) is added to a 250 ml flask equipped with argon purge, mechanical stirrer, oil bath, and vacuum line. The temperature is raised to 180° C. while stirring under an argon purge. After two hours, the pressure is reduced to 76 microns, the temperature is raised to 240° C. and the reaction is continued for 2 hours.

Example 2

Synthesis of co-poly-{[propyleneterephthalate]$_{40}$-[hexylenesebacinate]$_{60}$}

Dimethylsebacate (68.31 g, 0.297 mole), 1,6-hexanediol (35.05 g, 0.297 mole), and titanium tetrabutoxide (0.1 g, 2.94×10$^{-4}$ mole) is added to a 250 ml flask equipped with argon purge, mechanical stirrer, oil bath, and a vacuum line. The temperature is raised to 180° C. under an argon purge. The pressure is reduced to 76 microns, and the stirring continues for two hours. The mixture is purged with argon to atmospheric pressure, and dimethylterephthalate (37.67 g, 0.1942 mole) and 1,3-propanediol (14.76 g, 0.1942 mole) are added. Vacuum is restored to 76 microns, the temperature is raised to 240° C., and the reaction is continued for 2 hours.

Example 3

A first composition can be prepared by mixing the following components:
  (a) about 2.0% (w/w) of the polymer of Example 1; and
  (b) the balance is a 50/50 (w/w) blend of chloroform and 1,1,2-trichloroethane.

The first composition can be applied onto the surface of bare 12 mm small VISION™ stent (Guidant Corp.). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied at per one spray pass. Between the spray passes the stent can be dried for about 10 seconds in a flowing air stream at about 50° C. About 110 μg of wet coating can be applied. The stents can be baked at about 80° C. for about one hour, yielding a primer layer composed of approximately 100 μg of the polymer of example 1.

A second composition can be prepared by mixing the following components:
  (a) about 2.0% (w/w) of the polymer of Example 2;
  (b) about 0.5% (w/w) of paclitaxel; and
  (c) the balance is a 50/50 (w/w) blend of chloroform and 1,1,2-trichloroethane.

The second composition can be applied onto the dried primer layer to form the drug-polymer layer, using the same spraying technique and equipment used for applying the primer layer. About 160 μg of wet coating can be applied followed by drying and baking at about 50° C. for about 2 hours, yielding a dry drug-polymer layer having solids content of about 140 μg.

Example 4

A first composition can be prepared by mixing the following components:
(a) about 2.0% (w/w) of the polymer of Example 1; and
(b) the balance is a 50/50 (w/w) blend of chloroform and 1,1,2-trichloroethane. The first composition can be applied onto the surface of bare 12 mm small VISION™ stent (Guidant Corp.). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied at per one spray pass. About 110 μg of wet coating can be applied, and the stent can be dried for about 10 seconds in a flowing air stream at about 50° C. between the spray passes. The stents can be baked at about 80° C. for about one hour, yielding a primer layer composed of approximately 100 μg of the polymer of Example 1.

A second composition can be prepared by mixing the following components:
(a) about 2.0% (w/w) of the polymer of Example 1;
(b) about 1.0% (w/w) everolimus; and
(c) the balance is a 50/50 (w/w) blend of chloroform and 1,1,2-trichloroethane.

The second composition can be applied onto the dried primer layer to form the drug-polymer layer using the same spraying technique and equipment used for applying the primer layer. About 190 μg of wet coating can be applied followed by drying and baking at about 50° C. for about 2 hours, yielding a dry drug-polymer layer having solids content of about 170 μg.

A third composition can be prepared by mixing the following components:
(a) about 2.0% (w/w) the polymer of Example 1; and
(b) the balance is a 50/50 (w/w) blend of chloroform and 1,1,2-trichloroethane.

The third composition can be applied onto the dried drug-polymer layers to form a topcoat layer using the same spraying technique and equipment used for applying the primer and drug-polymer layers. About 110 μg of wet coating can be applied followed by drying and baking at about 50° C. for about 2 hours, yielding a dry topcoat layer having solids content of about 100 μg.

Example 5

Method of Preparing a Hydroxyl-terminated Polyester

Synthesis of co-poly-{[hexyleneterephthalate]$_{22}$-[hexylenesebacinate]$_{78}$} with Hydroxyl Endgroups Dimethylterephthalate (15.65 g, 0.0807 mole), 1,6-hexanediol (42.76 g, 0.3624 mole), dimethylsebacate (64.79 g, 0.2817 mole), and titanium tetrabutoxide (0.12 g, 3.53×10$^{-4}$ mole) is added to a 500 ml flask equipped with argon purge, mechanical stirrer, oil bath, and vacuum line. The temperature is raised to 180° C. while stirring under an argon purge. After two hours, the pressure is reduced to 76 microns, the temperature is raised to 240° C. and the reaction is continued for 2 hours. The reaction is purged with argon, cooled to ambient temperature, and 250 ml of 1,1,2-trichloroethane added. After dissolution, cyclohexylcarbodiimide (1.03 gm, 0.005 mole), 4-(dimethylamino)pyridinium-4-toluene sulfonate (0.16 gm, 0.54 mmole), and 1,6-hexanediol (1.18 gm, 0.01 mole) are added and stirred under argon for 48 hours. The polymer is isolated by precipitation into 1 liter of methanol followed by filtration.

Example 6

Method of Preparing a Carboxyl-terminated Polyester

Synthesis of Co-poly-{[Hexyleneterephthalate]$_{22}$-[Hexylenesebacinate]$_{78}$} with Carboxyl Endgroups Dimethylterephthalate (15.65 g, 0.0807 mole), 1,6-hexanediol (42.76 g, 0.3624 mole), dimethylsebacate (64.79 g, 0.2817 mole), and titanium tetrabutoxide (0.12 g, 3.53×10$^{-4}$ mole) is added to a 500 ml flask equipped with argon purge, mechanical stirrer, oil bath, and vacuum line. The temperature is raised to 180° C. while stirring under an argon purge. After two hours, the pressure is reduced to 76 microns, the temperature is raised to 240° C. and the reaction is continued for 2 hours. The reaction is purged with argon, cooled to ambient temperature, and 250 ml of 1,1,2-trichloroethane added. After dissolution, succinic anhydride (0.5 gm, 0.005 mole), is added and stirred under argon for 48 hours. The polymer is isolated by precipitation into 1 liter of methanol followed by filtration.

Example 7

Method of Preparing an Amino-terminated Polyester

Synthesis of Co-poly-{[Hexyleneterephthalate]$_{22}$-[Hexylenesebacinate]$_{78}$} with Amino Endgroups Dimethylterephthalate (15.65 g, 0.0807 mole), 1,6-hexanediol (42.76 g, 0.3624 mole), dimethylsebacate (64.79 g, 0.2817 mole), and titanium tetrabutoxide (0.1 g, 2.94×10$^{-4}$ mole) is added to a 500 ml flask equipped with argon purge, mechanical stirrer, oil bath, and vacuum line. The temperature is raised to 180° C. while stirring under an argon purge. After two hours, the pressure is reduced to 76 microns, the temperature is raised to 240° C. and the reaction is continued for 2 hours. The reaction is purged with argon, 250 ml of dry 1,1,2-trichloroethane added and the temperature reduced to 60° C. After dissolution, 1,4-diisocyantobutane (0.7 gm, 0.005 moles) and 1 gm of a 5% (w/w) solution of stannous octoate in 1,1,2-trichloroethane is added and the reaction stirred for 2 hours. After quenching the reaction with 25 ml of deionized water, it is stirred for an hour at ambient temperature and the polymer isolated by precipitation into 1 liter of methanol followed by filtration.

Example 8

A polyester of formula (X) can be prepared according to the following procedure:

Method of Preparing a Benzyl Ester of a Polycarboxylic Acid

Trimellitic acid (203.8 gm, 0.97 mole), p-toluenesulfonic acid (47.55 gm, 0.25 mole), benzyl alcohol (100.9 ml, 0.97 mole), and 200 ml of benzene is added to a 1 liter reaction flask equipped with a mechanical stirrer, Dean Stark trap, thermometer and argon inlet. The mixture is heated to 80° C. for 8 hours, and the water generated is collected in the Dean Stark trap. The mixture is transferred to a 2 liter flask, and 1 liter of ethyl acetate is added to the mixture with stirring. The mixture is stored overnight at 4° C., and the slurry is poured into 2 liters of deionized water. The mono-benzyl ester of trimellitic acid is isolated by filtration.

Method of Preparing a Graft Copolymer of a Polyester and an mPEG Amide

A polyester is prepared by adding 0.066 equivalents of a mono-benzyl ester of trimellitic acid, one equivalent of sebacic acid, 1.066 equivalents of 1,6-hexanediol and 0.20 equivalents of p-toluenesulfonic acid. The mixture can be dissolved in a suitable solvent such as, for example, benzene, toluene, 1,1,2-trichloroethane, or chlorobenzene. The mixture is then heated to reflux and the water generated is removed by azeotropic distillation using a Dean-Stark trap.

The polymer is precipitated in methanol, washed with water, and vacuum dried. A free carboxyl group is generated by hydrogenolysis over a palladium catalyst. Tetrahydrofuran (1200 ml) and the polymer (100 gm) are added to a 2 liter flask with a palladium on carbon catalyst (5 gm) (Aldrich). Hydrogen is bubbled and stirred through the mixture for 24 hours, and the palladium on carbon catalyst is separated by centrifugation to leave an isolated solution.

The isolated solution is added to hexane/ethyl acetate (10 liters of a 50/50 mixture) with stirring to precipitate the polyester. The polymer is filtered, dissolved (50 gm) in THF (1500 ml) in a 2 liter flask with stirring and an argon purge, and then combined with N-hydroxysuccinimide (1.38 gm, 0.012 mole) and dicyclohexylcarbodiimide (2.48 gm, 0.012 mole). The combination is stirred for 24 hours at ambient temperature and filtered to remove 1,3-dicyclohexylurea. The filtered solution is combined with an amino-terminated mPEG (MW 5000, 54.5 gm, 0.0109 moles) (Nektar Corp.) in a 2 liter flask and stirred for 6 hours under argon. The graft copolymer of the polyester and the mPEG, an amide graft, is precipitated by slow addition of the solution into hexane/ethyl acetate (50/50) with stirring.

Example 9

The polyester of formula (XIII) can be prepared according to the following procedure:

Method of Preparing a Graft Copolymer of a Polyester and 4-carboxy-TEMPO

A polyester is prepared by adding 0.25 equivalents of a mono-benzyl ester of trimellitic acid, one equivalent of adipic acid, 1.25 equivalents of 1,6-hexanediol, and 0.20 equivalents of p-toluenesulfonic acid. The mixture can be dissolved in a suitable solvent such as, for example, benzene, toluene, 1,1, 2-trichloroethane, or chlorobenzene. The mixture is then heated to reflux and the water generated is removed by azeotropic distillation using a Dean-Stark trap.

The polymer is separated, washed with water, and vacuum dried. A free carboxyl group is generated by hydrogenolysis over a palladium catalyst. Chlorobenzene (1200 ml) and the polymer (100 gm) are added to a 2 liter flask with a palladium on carbon catalyst (5 gm) (Aldrich). Hydrogen is bubbled and stirred through the mixture for 24 hours, and the palladium on carbon catalyst is separated by centrifugation to leave an isolated solution.

The isolated solution is added to hexane/ethyl acetate (10 liters of a 50/50 mixture) with stirring to precipitate the polyester. The polymer (50 gm) is filtered, dissolved and stirred in dry dimethylformamide (1500 ml) in a 2 liter flask, and acetic anhydride (4.77 gm, 0.0467 mole) and 4-carboxy-TEMPO (9.35 gm, 0.0467 mole) is added to the 2 liter flask. The mixture is distilled under vacuum to remove DMF at 80° C. and a sufficient amount of heat is applied to achieve a distillation rate of about 5 ml/min. The solution is heated and stirred for two hours. After approximately 60 ml of DMF is collected, the solution is cooled to room temperature, and purged with argon to ambient pressure. The graft copolymer of the polyester and the 4-carboxy-TEMPO, with an anhydride linkage, is precipitated by slow addition of the solution to anhydrous hexane/ethyl acetate (4 liters, 50/50) with stirring.

Example 10

The polyester of formula (XIV) can be prepared according to the following procedure:

Method of Preparing Conjugate of Estradiol and 3,9-Diethylidene-2,4,8,10-Tetraoxaspiro-[5,5]-Undecane (DETOSU)

Dry THF (40 ml) is combined with DETOSU (5 gm, 0.0236 mole) and six drops of 1% p-toluenesulfonic acid in THF in a 100 ml flask. A solution of estradiol (6.42 gm. 0.0236 mole) in THF (20 ml) is slowly added with stirring for over an hour. The estradiol-DETOSU conjugate is isolated by rotary evaporation.

Method of Preparing a Graft Copolymer of a Polyester and Estradiol

A polyester is prepared by adding 0.05 equivalents 1,3-dihydroxyacetone dimer, one equivalent of adipic acid, and 0.9 equivalents of 1,4-butanediol, and 0.20 equivalents of p-toluenesulfonic acid. The mixture can be dissolved in a suitable solvent such as, for example, benzene, toluene, 1,1, 2-trichloroethane, or chlorobenzene. The mixture is then heated to reflux and the water generated is removed by azeotropic distillation using a Dean-Stark trap. The polymer is isolated by precipitation into methanol, washed with water, and dried under a vacuum.

The polymer (100 gm), dry THF (500 ml), sodium cyanoborohydride (3.46 gm, 0.055 mole), and p-toluenesulfonic acid (2 drops of a 1% solution) in THF is added to a 1000 ml flask. The mixture is stirred for two hours at ambient temperature, poured into chloroform (1000 ml), and extracted with 3 portions of aqueous sodium bicarbonate (500 ml, 1M portions). Chloroform is removed by rotoevaporation and the remaining solvent is removed by drying overnight in a vacuum oven at ambient temperature. The polymer (60 gm), dry THF (250 ml), and the estradiol-DETOSU conjugate (14.54 gm, 0.03 mole) is added to a 500 ml flask and stirred at room temperature for two hours. The polymer is precipitated by slow addition of the solution into anhydrous hexane/ethyl acetate (2 liters, 90/10) with stirring.

Example 11

Method of Preparing a Polyester-heparin Conjugate by Combining Heparin with an Amino-terminated Polyester A polyester-heparin conjugate can be prepared by reacting an amino-terminated polyester with a aldehyde-functionalized heparin formed by oxidative cleavage of heparin. An amino-terminated polyester (50 g) is added to a reactor containing DMAC/water (1 liter, 40:1) under nitrogen. An aldehyde-functionalized heparin (7.5 g) and sodium cyanoborohydride (0.2 g; 3.2 mmol) is added to the solution and heated to 40° C. for 24 hours under nitrogen, cooled to room temperature, and added dropwise to methanol. The polyester-heparin conjugate is filtered, washed with 3 portions of water (250 mL portions), and dried under vacuum.

Alternate Method of Preparing a Polyester-heparin Conjugate by EDC Coupling of a D-glucoronic Acid or L-iduronic Acid Functionality of the Heparin in a DMAC/Water Medium Heparin (20 g) and an amino-functional polyester (50 g) is added to a DMAC/water solution (40/1; 450 g) and dissolved. The pH is adjusted to 4.75 and N-(3'-dimethylaminopropyl)-N'-ethylcarbodiimide (0.2 g, 1.0 mmol) is added. The solution is stirred at room temperature for 24 hours under nitrogen. The solution is neutralized with sodium hydroxide (0.1 M) to pH 7.5 and stirred overnight under nitrogen. The polyester-heparin conjugate is precipitated by addition of the solution into THF, filtered and washed with water.

Example 12

Method of Preparing a Polyester-PEG Conjugate with an Amino-terminated Polyester An amino-terminated polyester can be PEGylated by reductive amination with an aldehyde terminated PEG, carbodiimide coupling of a carboxyl terminated PEG, or maleimide coupling of a PEG-maleimide to an amine terminated polyester.

An amino-terminated polyester can be conjugated to PEG by reductive amination. A PEG-butyraldehyde with a free aldehyde group made by reductive amination of an amino-PEG with an excess of butyraldehyde. An amino-terminated polyester (50 g) is dissolved in anhydrous DMAC (230 g), and the PEG-butyraldehyde (MW 1000-50,000, 7.5 g) is added with sodium cyanoborohydride (1.0 g), and stirred overnight at room temperature under nitrogen. The polymer is precipitated by addition of the solution with stirring in methanol, redissolved in DMAC, reprecipitated in water, and dried under vacuum.

An amino-terminated polyester can be conjugated to PEG by carbodiimide coupling of a carboxyl terminated PEG using DCC/NHS coupling. Anhydrous THF (100 g), carboxyl-terminated PEG (10 kD, 7.0 g, 0.7 mmol), and dicyclohexylcarbodiimide (0.15 g; 7.1 mmol) (DCC) is added to a reactor containing N-hydroxysuccinimide (0.10 g/8 mmol) (NHS), and the solution stirred at ambient temperature for 12 hours under nitrogen. An amino-terminated polyester (50 g) is added to anhydrous THF (116 g; 1-35% w/w). The mixture is stirred under nitrogen for 2 hours at room temperature to dissolve the polyester, and the amino-terminated polyester solution is added to the activated PEG solution in a dropwise manner, and stirred overnight at room temperature under nitrogen. The PEG-polyester is isolated by adding dropwise to 1 liter of methanol to form a polyester-PEG precipitate. The precipitate is filtered and dried under vacuum.

Example 13

A medical article with two layers of coating can be fabricated to comprise everolimus by preparing a first composition and a second composition, wherein the first composition can be an agent layer comprising a matrix of a polyester and agent, and the second composition can be a polyester topcoat layer.

The first composition can be prepared by mixing a functionalized polyester with the everolimus in a THF/1,1,2-trichloroethane blend, sprayed onto a surface of a bare 12 mm VISION™ stent (Guidant Corp.) ("example stent"), and dried to form a coating. An example coating technique comprises spray-coating with a 0.014 fan nozzle, a feed pressure of about 0.2 atm and an atomization pressure of about 1.3 atm; applying about 20 µg of wet coating per pass; drying the coating at about 50° C. for about 10 seconds between passes and baking the coating at about 50° C. for about 1 hour after the final pass to form a dry agent layer. The second composition can be prepared by mixing the polyester in a THF/1,1,2-trichloroethane blend and applying the polyester using the example coating technique.

Example 14

A medical article with three layers of coating can be fabricated to comprise everolimus by preparing a first composition, a second composition and a third composition. The first composition can be a primer layer of a polyester. The second composition can be a pure agent layer, and the third composition can be a topcoat layer of a polyester.

The first composition can be prepared by mixing about 2% (w/w) of the polyester in a THF/1,1,2-trichloroethane blend and applied onto the surface of the example stent using the example coating technique to form a dry primer layer. The dry primer layer can contain about 100 µg of the polyester. The second composition can be prepared by mixing about 2% (w/w) everolimus in absolute ethanol and applying mixture to the primer layer using a coating technique to form a pure agent layer comprising of everolimus. The third composition can be prepared by mixing about 2% (w/w) of the polyester in a THF/1,1,2-trichloroethane blend and applying the mixture using a coating technique to form a topcoat layer comprising the polyester.

Example 15

Carboxyl-terminated polyesters can also be prepared in these embodiments by several methods. In one method, an activated dicarboxylic acid compound such as, for example, a diacid chloride or di-p-nitrophenyl sebacinate, can be combined with the polyester in excess. This method is simple, but it has a potential drawback of lowering the final molecular weight of the polymer.

Method of Preparing a Hydroxyl-terminated Co-poly-{[Butylenesebacinate]$_{50}$-[Cyclohexyldimethylsebacinate]$_{50}$}

Dry triethylamine (61.6 ml, 0.44 mole) is added to a mixture of cyclohexanedimethanol (14.42 gm, 0.1 mole), and 1,4-butanediol (9.01 gm, 0.1 mole), in dry THF (110 ml). The mixture is cooled to 0° C. and a solution of sebacoyl chloride (47.83 gm, 0.2 mole) in THF (100 ml) is added dropwise with stirring. The solution is stirred at 0° C. for 4 hours, at which point 1,3-propanediol (1.52 gm, 0.02 mole) is added and the mixture is allowed to warm to ambient temperature and stirred for an additional hour. The solution is diluted with acetone (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotary evaporation, and the hydroxy-terminated co-poly-{[butylenesebacinate]$_{50}$-[cyclohexyldimethylsebacinate]$_{50}$} is dried overnight in a vacuum oven at ambient temperature.

Method of Preparing a Carboxy-terminated Co-poly-{[Butylenesebacinate]$_{50}$-[Cyclohexyldimethylsebacinate]$_{50}$}

Dry triethylamine (61.6 ml, 0.44 mole) is added to a mixture of cyclohexanedimethanol (14.42 gm, 0.1 mole), and 1,4-butanediol (9.01 gm, 0.1 mole), in dry THF (110 ml). The mixture is cooled to 0° C. and a solution of sebacoyl chloride (47.83 gm, 0.2 mole) in THF (100 ml) is added dropwise with stirring. The solution is stirred at 0° C. for 4 hours, at which point succininc anhydride (2 gm, 0.02 mole) is added and the mixture is allowed to warm to ambient temperature and stirred for an additional hour. The solution is diluted with acetone (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotary evaporation, and the hydroxyl-terminated co-poly-{[butylenesebacinate]$_{50}$-[cyclohexyldimethylsebacinate]$_{50}$} is dried overnight in a vacuum oven at ambient temperature.

This polymerization can result in a polymer wherein some of the endgroups are carboxyl, and some of the endgroups are still in the form of an acid chloride. However, these will be hydrolyzed to carboxyl groups by the aqueous extractions.

While particular embodiments of the present invention have been shown and described, those skilled in the art will note that variations and modifications can be made to the present invention without departing from the spirit and scope the teachings. For example, a multitude of chemical structures, polymers, agents and methods have been taught herein. One of skill in the art is to appreciate that such teachings are provided by way of example only and are not intended to limit the scope of the invention. For example, the chemical structures taught herein are meant to cover all geometries possible for each chemical structure illustrated rather than to depict any particular geometry such as, for example, a particular stereoisomer, unless otherwise specified.

We claim:

1. A medical article comprising a polymer formed by reaction of a polyol and a polycarboxylic acid, the polymer comprising a structure of a formula:

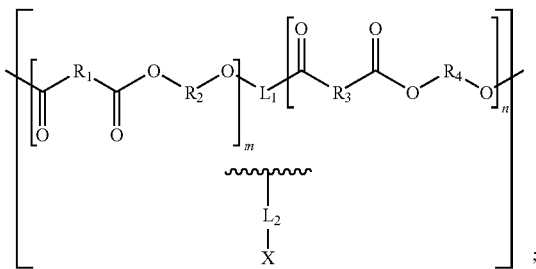

wherein
$R_1$ and $R_3$ are different from each other and each comprises a component selected from a group consisting of a chemical bond, substituted, unsubstituted, hetero-, straight-chained, branched, cyclic, saturated or unsaturated aliphatic radicals, and substituted, unsubstituted, or heteroaromatic radicals;

$R_2$ and $R_4$ each comprises a component independently selected from a group consisting of substituted, unsubstituted, hetero-, straight-chained, branched, cyclic, saturated and unsaturated aliphatic radicals; and substituted, unsubstituted, and heteroaromatic radicals;

the grouping

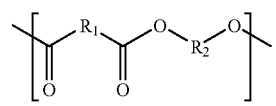

is derived from polyacid HOOC—$R_1$—COOH and diol HO—$R_2$—OH;

the grouping

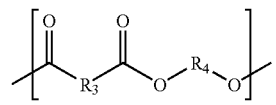

is derived from polyacid HOOC—$R_3$—COOH and diol HO—$R_4$—OH;

polyacid HOOC—$R_1$—COOH and polyacid HOOC—$R_3$—COOH are each an aliphatic dicarboxylic acid independently selected from the group consisting of oxalic acid, malonic acid, glutaric acid, adipic acid, pimelic acid, suberic acid, azelaic acid, sebacic acid, undecanedioic acid, dodecandioic acid, tridecanedioic acid, tetradecanedioic acid, petadecanedioic acid, hexadecanedioic acid, citric acid, maleic acid and fumaric acid;

$L_1$ is a chemical bond or a linkage;

X is an agent;

$L_2$ is an optional linkage connecting X to the polymer; and m and n are integers not equal to 0.

2. The medical article of claim 1, wherein $R_1$ or $R_3$ comprises an aromatic radical.

3. The medical article of claim 2, wherein the aromatic radical comprises a component selected from the group consisting of p-phenylene, m-phenylene, o-phenylene, and derivatives thereof.

4. The medical article of claim 1, wherein
$R_1$ comprises a phenylene radical or a derivative thereof;
$R_2$ and $R_4$ each comprises a component derived from a diol independently selected from a group consisting of 1,3-propanediol, 1,4-butanediol, 1,6-hexanediol, and derivatives thereof; and
$R_3$ comprises a component derived from a diacid selected from a group consisting of adipic acid, pimelic acid, suberic acid, azelaic acid, sebacic acid, and derivatives thereof.

5. The medical article of claim 1, wherein X comprises poly(ethylene glycol), poly(N-vinyl pyrrolidone), phosphorylcholine, hyaluronic acid, heparin, hirudin, or any derivatives, analogs, homologues, congeners, salts, copolymers or combinations thereof.

6. The medical article of claim 1, wherein X comprises a component selected from a group consisting of a free radical scavenger, a nitric oxide donor, rapamycin, everolimus, tacrolimus, paclitaxel, docetaxel, estradiol, clobetasol, idoxifen, tazarotene and any prodrugs, metabolites, analogs, homologues, congeners, and any derivatives, salts and combinations thereof.

7. The medical article of claim 6, wherein the free radical scavenger comprises a component selected from a group consisting of 2,2',6,6'-tetramethyl-1-piperidinyloxy free radical; 4-amino-2,2',6,6'-tetramethyl-1-piperidinyloxy free radical; 4-hydroxy-2,2',6,6'-tetramethyl-piperidene-1-oxy free radical; 2,2',3,4,5,5'-hexamethyl-3-imidazolinium-1-yloxy methyl sulfate free radical; 16-doxyl-stearic acid free radical; superoxide dismutase mimic; and any analogs, homologues, congeners, derivatives, salts and combinations thereof.

8. The medical article of claim 6, wherein the nitric oxide donor comprises a component selected from the group consisting of S-nitrosothiols, nitrites, N-oxo-N-nitrosamines, substrates of nitric oxide synthase, diazenium diolates and any analogs, homologues, congeners, derivatives, salts and combinations thereof.

9. The medical article of claim 1, wherein $L_1$ and $L_2$ each comprise a component selected from a group consisting of amides, esters, anhydrides, orthoesters, all-aromatic carbonates, ureas, urethanes, semicarbazones, imines, oximes, ketals, acetals, disulfides, and a combination thereof.

10. The medical article of claim 1, which is a stent.

11. The medical article of claim 1, wherein the polymer is a included in a coating on the medical article.

12. The medical article of claim 11, which is a stent.

* * * * *